(12) United States Patent
Howard

(10) Patent No.: US 7,100,707 B2
(45) Date of Patent: Sep. 5, 2006

(54) STABILIZED SOIL CORE SAMPLES AND METHOD FOR PREPARING SAME

(76) Inventor: Harold Howard, 1509 E. Piute, Phoenix, AZ (US) 85024

( * ) Notice: Subject to any disclaimer, the term of this patent is extended or adjusted under 35 U.S.C. 154(b) by 317 days.

(21) Appl. No.: 10/759,874

(22) Filed: Jan. 16, 2004

(65) Prior Publication Data

US 2005/0155793 A1    Jul. 21, 2005

(51) Int. Cl.
*E21B 49/00* (2006.01)
(52) U.S. Cl. .................. 175/20; 175/226; 73/432.1; 73/864.51
(58) Field of Classification Search .............. 175/58, 175/20, 226; 73/864.51, 432.1
See application file for complete search history.

(56) References Cited

U.S. PATENT DOCUMENTS

| | | | |
|---|---|---|---|
| 1,109,446 A | | 9/1914 | Melberg |
| 2,880,969 A | * | 4/1959 | Williams .................. 175/226 |
| 2,982,704 A | * | 5/1961 | Shelton et al. .............. 205/159 |
| 3,013,607 A | * | 12/1961 | Bond et al. .................. 166/269 |
| 3,176,769 A | * | 4/1965 | Treadway et al. .......... 166/295 |
| 3,324,563 A | * | 6/1967 | De Gast ...................... 33/304 |
| 3,631,934 A | * | 1/1972 | Mendes da Rocha ......... 175/58 |
| 4,071,099 A | | 1/1978 | Hensel |
| 4,587,857 A | | 5/1986 | Bush |
| 4,653,336 A | | 3/1987 | Vollweiler |
| 4,809,790 A | | 3/1989 | Manchak |
| 4,848,484 A | | 7/1989 | Clements |
| 5,360,074 A | | 11/1994 | Collee |
| 5,560,438 A | | 10/1996 | Collee |
| 2004/0035607 A1 | * | 2/2004 | Jacobs et al. .................. 175/20 |

* cited by examiner

*Primary Examiner*—David Bagnell
*Assistant Examiner*—Daniel P Stephenson
(74) *Attorney, Agent, or Firm*—LaValle D. Ptak

(57) ABSTRACT

An intact core sample from a soil area, such as a golf green or a ball field, is embedded in molded plastic. The core sample first is obtained, and then adhesively bonded together prior to molding it in clear plastic to preserve the soil core sample in an intact and durable fashion for subsequent visual examination of the composition of the soil core sample.

22 Claims, 2 Drawing Sheets

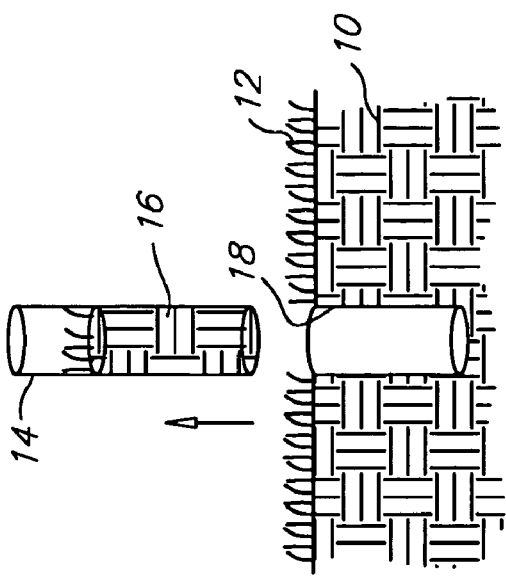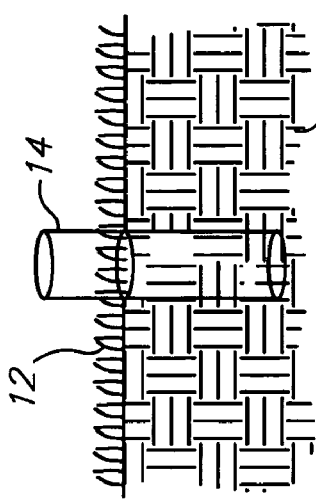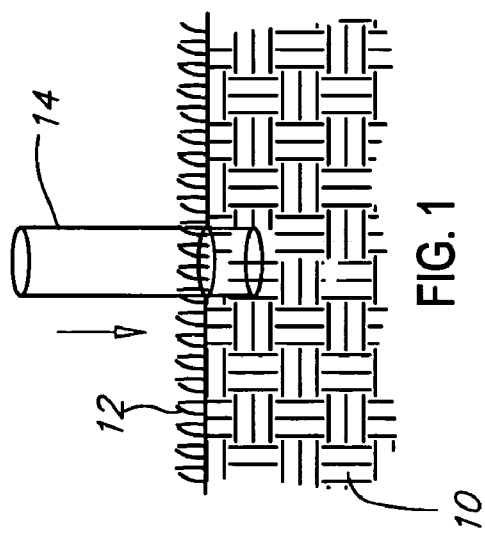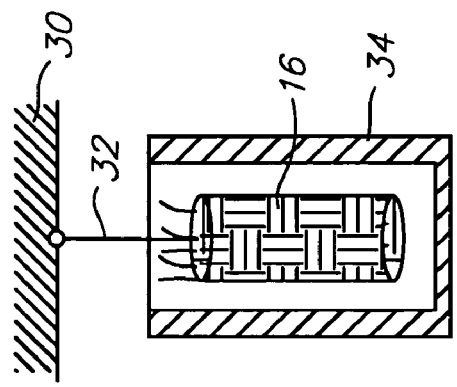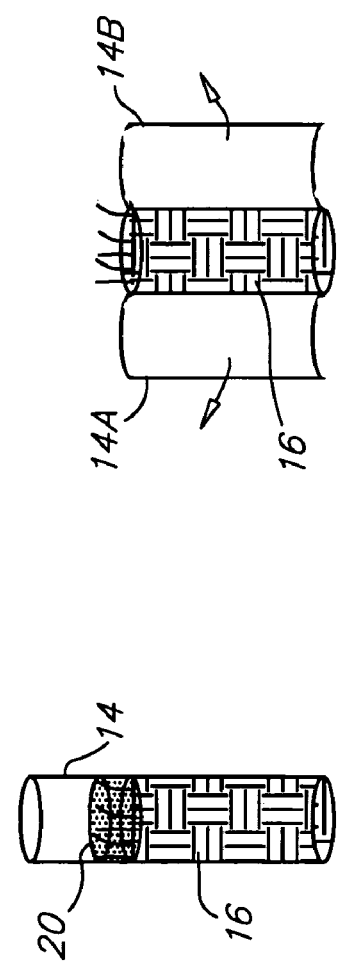

STABILIZED SOIL CORE SAMPLES AND METHOD FOR PREPARING SAME

BACKGROUND

In the development and maintenance of turf grass areas, such as golf greens or baseball and football fields, the composition of the underlying soil plays a significant part in the health and characteristics of the turf grass. In the original development of grass areas and in the subsequent monitoring of such areas for maintenance purposes, soil core samples are taken for analysis by experts to determine the proper nutrients to be used, watering amounts and intervals, as well as possible replacement or modification of particular areas, depending upon the characteristics of the soil core sample. It also is desirable, over the life of a golf green or a ball field, periodically to obtain samples from the same area of the field to determine how the soil composition changes over time to determine whether or not soil replacement or particular soil enhancement steps should be taken.

An early patent directed to the obtaining of soil core samples is the Melberg U.S. Pat. No. 1,109,446. This patent discloses a cutting tool which is pressed into the soil, and which includes an outer metal cutting core with an interior sample glass receiving tube in it. The core sample is pressed upwardly into the glass tube; and after the sample has been withdrawn, a cork or sealing device is placed in the upper open end of the glass tube. The entire unit then is inverted; and the glass tube is removed from the outer cutting tube. The other end of the glass tube then is closed; and the soil core sample may be stored and viewed at a subsequent time. It should be noted that there is nothing in the device or method of Melberg which stabilizes the position of the various components of the soil sample within the tube.

The Vollweiler U.S. Pat. No. 4,653,336 is directed to a combination soil auger and soil core sampler, which in many aspects is similar to that of the Melberg patent. In Vollweiler, the interior cylindrical soil-retaining insert is disclosed as being made of a variety of materials, including thermoplastic materials and stainless steel. Obviously, if materials which are not transparent are employed, it is necessary to remove the soil sample from the sample retaining insert in order to examine it. In all other respects, the disclosure of the Vollweiler patent is similar to that of Melberg.

The Bush U.S. Pat. No. 4,587,857 is directed to a method for mounting or stabilizing relatively unstable core samples from an oil drilling bore hole. The sample is obtained in a conventional manner by the drilling apparatus. The sample then is inserted into a length of heat shrinkable tubing. End plugs are inserted at each end of the sample; and the tubing is heated to cause it to shrink onto and to conform to the outer circumferential surface of the core sample. The tubing is cut off at the opposite ends of the core sample (which have had plugs inserted into them previously), and the entire assembly then is frozen prior to cutting off or squaring the ends and mounting the sample for subsequent viewing.

The Hensel U.S. Pat. No. 4,071,099 also is directed to a method for preserving a core sample from an oil well core. In the Hensel device, the core sample is encased, during the coring operation, into a rubber sleeve. Subsequently, the rubber sleeve is frozen. The sleeve then is placed in an elongated horizontal form and is cast around the greater portion of its circumference. An exposed portion of the rubber sleeve then may be cut away to expose the core for subsequent viewing and testing. The device and method of this patent is fairly complex; and it is not a simple hand operated method and apparatus.

The Clements U.S. Pat. No. 4,848,484 is directed to a hand operated soil extraction tool which has a pivoting door extending substantially along the length of it; so that a withdrawn sample can be directly viewed in the tool after the sample has been removed.

The Manchak U.S. Pat. No. 4,809,790 is an oil core device which freezes the core in place prior to its removal from the ground. Once again, this is a complex system and method for obtaining an intact core sample.

Two additional United States patents directed to oil drilling apparatus for obtaining samples from deep within the earth are Collee U.S. Pat. Nos. 5,360,047 and 5,560,438. These patents are based on the same disclosure, and disclose a technique for encasing a core sample as it is being obtained. This is done by inserting a gel material into the core sample; and the gel material is designed to solidify at temperatures slightly lower than those expected down-hole. As the core sample is withdrawn, the gel-like material solidifies to encapsulate the core to maintain its integrity during withdrawal and during subsequent transportation.

It is desirable to provide an apparatus and method for obtaining and preserving core samples which maintains the integrity of the sample in a simple and efficient manner, and which preserves the sample for subsequent visual observation over an indefinite period of time.

SUMMARY OF THE INVENTION

It is an object of this invention to provide an improved method for mounting a soil core sample.

It is an additional object of this to provide an improved mounted soil core sample.

It is another object of this invention to provide an improved method for obtaining and preserving a soil core sample.

It is a further object of this invention to provide an improved method for obtaining and mounting a soil core sample which first preserves the integrity of the soil core sample, and then subsequently encapsulates the soil core sample in a clear plastic material.

In accordance with a preferred embodiment of the invention, a method for mounting a soil core sample includes the steps of obtaining the soil core sample in a length of hollow cylindrical pipe. The soil core sample then is bonded to stabilize it within the pipe prior to removing the soil core sample from the pipe. The bonded soil core sample then is molded in a clear plastic resin to provide a relatively permanent mounted soil core sample capable of transportation and subsequent visual inspection without disturbance of the soil core sample.

BRIEF DESCRIPTION OF THE DRAWINGS

FIGS. 1, 2 and 3 illustrate method steps taken in a preferred embodiment of the invention;

FIGS. 4, 5 and 6 illustrate method steps of a preferred embodiment of the invention;

DETAILED DESCRIPTION

Figure 7:
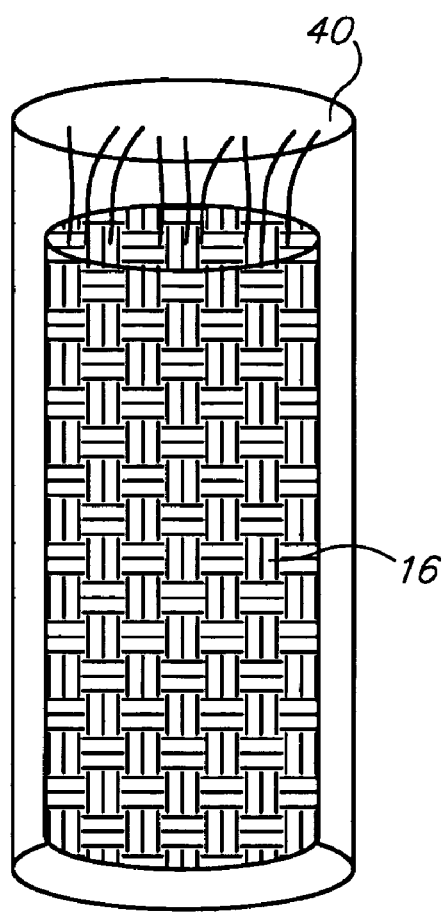
FIG. 7 is a perspective view of a preferred embodiment of the invention.

Reference now should be made to the drawings, in which the same reference numbers are used throughout the different figures to designate the same or similar components.

Reference first should be made to FIG. 1, which illustrates diagrammatically a cross section of a typical turf grass area 10, with grass 12 growing out of it, such as is used with golf greens or ball fields, or the like. It is desirable to obtain samples of the soil media 10 in which the grass 12 is rooted in order to perform analysis necessary to obtain the optimal growing conditions for the grass 12. To do this, in a preferred embodiment of the invention, a length of schedule 40 PVC pipe 14, approximately 24" long and having approximately a 2" diameter, is ground to a beveled edge at its bottom, and is pounded into the turf grass/root zone media 10 to the depth desired for sampling of the root zone media. This is illustrated in FIG. 1 by the downward arrow adjacent the section of pipe 14. It should be noted that the PVC pipe 14 is open at both ends.

Once the pipe 14 has been driven into the ground to the desired length, as shown in FIG. 2, it can be seen that the lower portion of the pipe 14 surrounds the depth of the root zone media or earth 10 which is to become the sample core, with a space of several inches between the top of the root zone media 10 and the open top of the pipe 14. As illustrated in FIG. 3, the pipe 14 then is withdrawn from the soil with a core sample 16 of the media 10 remaining inside the pipe. A core, such as the core sample 16, has been obtained with various types of implements in the past. The objective is to obtain a core sample 16 which is as undisturbed as possible. As illustrated in FIG. 3, the removal of the core sample 16 leaves a void 18 in the surrounding media 10.

As shown in FIG. 4, the next step is to thoroughly infiltrate the core sample 16 with a dilute adhesive solution 20. Preferably, adhesive is diluted in water; and the solution 20 is poured into the open top of the sampling pipe 14, as illustrated in FIG. 4. The adhesive solution 20 is allowed to completely permeate the core sample 16; and it bonds together the particles of the earth or root zone media to maintain their orientation during subsequent transportation, storage and observation. It has been found that a dilute solution of approximately 1 part latex carpenter's glue and 9 parts of water poured into the top of the pipe 15 in an amount in excess of the amount required to bond the particles of the core sample 16 together is effective. The excess adhesive solution 20 drains out of the open bottom of the pipe 14. Once the solution 20 has thoroughly impregnated the core sample 16, the sample 16 is frozen.

After freezing of the sample 16, the PVC pipe 14 is split longitudinally in any suitable manner, such as by sawing, at one or more points along its length. After the pipe 14 has been split, it is opened, forming at least two portions, 14A and 14B, by bending it away from the core sample 16, as shown in the arrows of FIG. 5. The bonded core sample 16 is removed from the opened pipe 14; and after it is thoroughly dried it may be handled carefully without disturbing its integrity.

The next step is shown in FIG. 6. The core sample 16, after drying and hardening, is suspended from a suitable support, such as the support 30 by means of a cord 32, or in some other manner, into a hollow cylindrical mold 34 which is open at the top and closed at the bottom, as clearly shown in FIG. 6. Based on the dimensions of the other components described above, the inside diameter of the mold is selected to be approximately 60 millimeters. The core sample is suspended coaxially within the mold 34, with approximately 1.5" of clearance at both the bottom and the top. By using a coaxial suspension in the cylindrical mold, the sample 16 is positioned equidistant from the interior of the side wall of the mold 34.

After the positioning of the core sample 16 as shown in FIG. 6, the mold 34 is filled with a catalyzed liquid plastic resin poured into the mold to place a layer of resin beneath, above and surrounding the core sample 16 which is suspended within the mold 34. After catalyzation or hardening of the plastic, the encapsulated core sample 16 is removed from the mold to result in the encapsulated product shown in FIG. 7, where a clear (transparent) hard plastic covering 40 completely encases the core sample 16 to allow undisturbed transportation and storage of the core sample 16, as well as ready visual inspection of the core sample through the relatively thin walls of the clear plastic 40 which encases the core sample. By encasing the core sample 16 in hardened clear plastic material, which may be any suitable material used to encapsulate various articles, the core sample is available for an indeterminate period of time for observation, comparison with core samples taken from the same area in different time periods or in different years; and it may be stored indefinitely.

Figure 8:
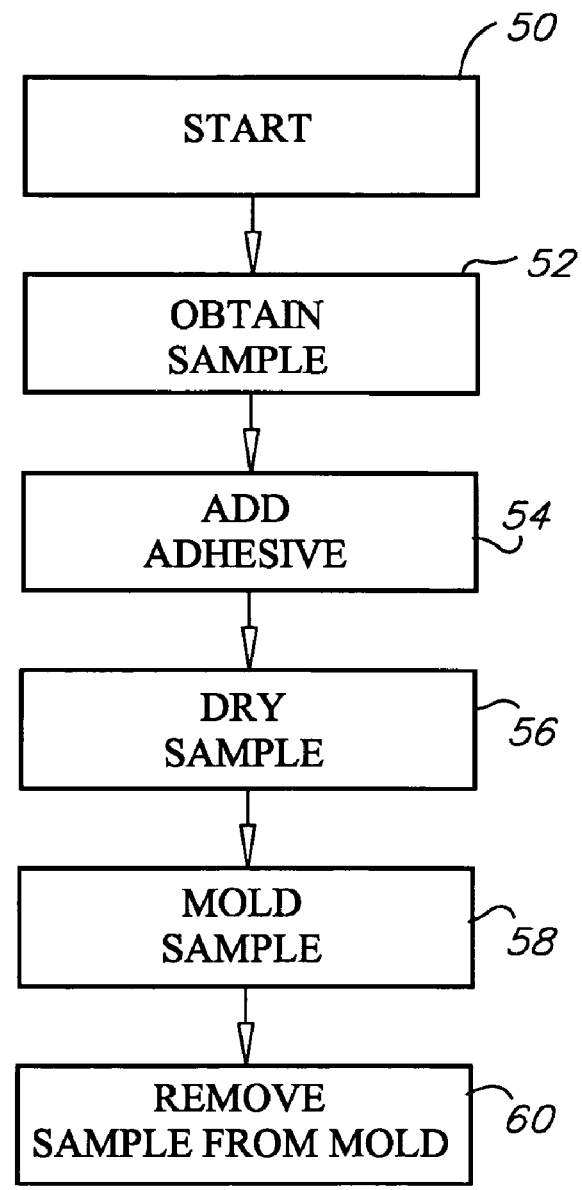
FIG. 8 is a flow chard of the method of a preferred embodiment of the invention.

FIG. 8 is a flow chart illustrating the manner in which the permanently encased core sample 16 is obtained. As shown in FIG. 8, the operation starts at 50 and the sample is obtained at 52, in accordance with the procedures set forth in FIGS. 1 through 3. At 54, adhesive is added as shown in FIG. 4; and at 56, the sample is dried. This is generally described in conjunction with FIG. 5 above. After the sample has been dried at 56, it is molded at 58, in accordance with the procedure described in conjunction with FIG. 6. After molding and hardening of the plastic, the sample is removed from the mold at 60 to form the completed product of an encapsulated core sample, as shown in FIG. 7.

The foregoing description of the preferred embodiment of the invention is to be considered as illustrative and not limiting. Various changes and modifications will occur to those skilled in the art for performing substantially the same function, in substantially the same way, to achieve substantially the same result, without departing from the true scope of the invention as defined in the appended claims.

What is claimed is:

1. A mounted soil core sample including in combination:
    a stabilized soil core sample, the particles of which are adhesively bonded together, having a cylindrical shape with a first predetermined diameter and a first predetermined length; and
    a plastic casing molded about the soil core sample in intimate physical contact therewith, the casing having an external diameter greater than the first predetermined external diameter of the soil core sample.

2. The mounted soil core sample according to claim 1 wherein the plastic casing is transparent.

3. The mounted soil core sample according to claim 2 wherein the plastic casing is a molded plastic casing fully enclosing the soil core sample.

4. The mounted soil core sample according to claim 3 wherein the plastic casing is made of a catalyzed plastic resin.

5. The mounted soil core sample according to claim 1 wherein the plastic casing is a molded plastic casing fully enclosing the soil core sample.

6. The mounted soil core sample according to claim 5 wherein the plastic casing is made of a catalyzed plastic resin.

7. The mounted soil core sample according to claim 1 wherein the plastic casing is made of a catalyzed plastic resin.

8. The mounted soil core sample according to claim 7 wherein the plastic casing is transparent.

9. A method of mounting a soil core sample including the steps of:
obtaining a soil core sample in a length of hollow cylindrical pipe;
bonding the elements of the soil core sample together within the pipe;
removing the bonded soil core sample from the pipe; and
molding clear plastic resin around the soil core sample.

10. The method of mounting a soil core sample according to claim 9 wherein the step of bonding the elements of the soil core sample together comprises adhesively bonding the elements of the core sample together.

11. The method according to claim 10 wherein the step of molding clear plastic resin around the soil core sample comprises molding clear plastic resin completely around the soil core sample.

12. The method according to claim 11 wherein the step of bonding the soil core sample comprises infiltrating the soil core sample within the pipe with an adhesive solution.

13. The method according to claim 12 wherein the step of molding clear plastic resin around the soil core sample includes suspending the bonded soil core sample within a mold and pouring catalyzed liquid resin into the mold to surround the soil core sample.

14. The method of mounting a soil core sample according to claim 13 including the further step of drying the soil core sample after infiltrating the soil core sample with an adhesive solution.

15. The method according to claim 9 wherein the step of bonding the soil core sample comprises infiltrating the soil core sample within the pipe with an adhesive solution.

16. The method of mounting a soil core sample according to claim 15 including the further step of drying the soil core sample after infiltrating the soil core sample with an adhesive solution.

17. The method according to claim 16 wherein the step of infiltrating the soil core sample within the pipe with an adhesive solution comprises infiltrating the soil core sample with a dilute solution of latex glue and water.

18. The method according to claim 17 wherein the step of removing the soil core sample from the pipe comprises splitting the pipe open to expose the bonded soil core sample.

19. A method according to claim 17 wherein the step of obtaining a soil core sample in a length of hollow cylindrical pipe comprises obtaining the soil core sample in a length of hollow PVC pipe and the step of removing the soil core sample from the pipe includes splitting the pipe longitudinally to separate the pipe from the soil core sample.

20. The method according to claim 9 wherein the step of molding clear plastic resin around the soil core sample includes suspending the bonded soil core sample within a mold and pouring catalyzed liquid resin into the mold to surround the soil core sample.

21. The method according to claim 9 wherein the step of molding clear plastic resin around the soil core sample comprises molding clear plastic resin completely around the soil core sample.

22. A method according to claim 9 wherein the step of obtaining a soil core sample in a length of hollow cylindrical pipe comprises obtaining the soil core sample in a length of hollow PVC pipe and the step of removing the soil core sample from the pipe includes splitting the pipe longitudinally to separate the pipe from the soil core sample.

* * * * *